US008609925B2

(12) United States Patent
Cheng et al.

(10) Patent No.: US 8,609,925 B2
(45) Date of Patent: *Dec. 17, 2013

(54) ADSORBENTS WITH IMPROVED MASS TRANSFER PROPERTIES AND THEIR USE IN THE ADSORPTIVE SEPARATION OF PARA-XYLENE

(75) Inventors: Linda Shi Cheng, Highland Park, IL (US); James A. Johnson, Clarendon Hills, IL (US)

(73) Assignee: UOP LLC, Des Plaines, IL (US)

( * ) Notice: Subject to any disclaimer, the term of this patent is extended or adjusted under 35 U.S.C. 154(b) by 822 days.

This patent is subject to a terminal disclaimer.

(21) Appl. No.: 12/165,412

(22) Filed: Jun. 30, 2008

(65) Prior Publication Data

US 2009/0326311 A1 Dec. 31, 2009

(51) Int. Cl.
*C07C 7/13* (2006.01)
*C07C 7/12* (2006.01)

(52) U.S. Cl.
USPC ............ 585/828; 585/820; 585/827; 585/826

(58) Field of Classification Search
USPC ......................................... 585/820, 827, 828
See application file for complete search history.

(56) References Cited

U.S. PATENT DOCUMENTS

| | | | | |
|---|---|---|---|---|
| 3,997,620 | A * | 12/1976 | Neuzil ........................... | 585/828 |
| 4,058,586 | A | 11/1977 | Chi et al. | |
| 4,415,481 | A * | 11/1983 | Smolin ........................... | 502/62 |
| 5,107,062 | A * | 4/1992 | Zinnen ........................... | 585/828 |
| 5,849,981 | A * | 12/1998 | Kulprathipanja ............. | 585/828 |
| 5,916,531 | A | 6/1999 | Pan | |
| 5,958,366 | A | 9/1999 | Smith et al. | |
| 6,706,938 | B2 * | 3/2004 | Roeseler et al. .............. | 585/820 |
| 6,723,155 | B2 | 4/2004 | Weyrich et al. | |
| 6,878,855 | B2 | 4/2005 | Deckman et al. | |
| 6,884,918 | B1 * | 4/2005 | Plee et al. ...................... | 585/828 |
| 7,300,899 | B2 | 11/2007 | Weston et al. | |
| 7,638,677 | B2 * | 12/2009 | Kulprathipanja ............. | 585/828 |
| 2005/0170947 | A1 * | 8/2005 | Plee et al. ....................... | 502/64 |
| 2008/0076952 | A1 * | 3/2008 | Kulprathipanja ............. | 585/826 |
| 2008/0138619 | A1 | 6/2008 | Miller | |

FOREIGN PATENT DOCUMENTS

| | | | |
|---|---|---|---|
| CN | 1448213 | * | 10/2003 |
| CN | 1565718 | * | 1/2005 |
| CN | 1565718 | A | 1/2005 |
| EP | 0 425 740 | A1 | 10/1989 |
| EP | 1 679 286 | A1 | 7/2006 |
| RU | 2283278 | C1 | 9/2006 |
| SU | 988766 | A1 | 1/1983 |
| WO | WO9526207 | A1 | 10/1995 |

OTHER PUBLICATIONS

Kulprathipanja, S., "Adsorbent and Process for the Separation of Meta-Xylene from Aromatic Hydrocarbons," pending U.S. Appl. No. 12/165,266.
Kulprathipanja, S., "Binderless Adsorbents Comprising Nano-Size Zeolite X and Their Use in the Adsorptive Separation of Para-Xylene," pending U.S. Appl. No. 12/165,329.
Cheng, Linda Shi, "Binderless Adsorbents with Improved Mass Transfer Properties and Their Use in the Adsorptive Separation of Para-Xylene," pending U.S. Appl. No. 12/165,359.
Priegnitz, James W., "Binderless Adsorbents and Their Use in the Adsorptive Separation of Para-Xylene," pending U.S. Appl. No. 12/165,390.
U.S. Appl. No. 12/165,390, filed Jun. 30, 2008, Priegnitz et al.
U.S. Appl. No. 12/165,359, filed Jun. 30, 2008, Cheng et al.
U.S. Appl. No. 12/165,329, filed Jun. 30, 2008, Kulprathipanja et al.
U.S. Appl. No. 12/165,266, filed Jun. 30, 2008, Kulprathipanja et al.
Zhang et al. "An Investigation of Knoevenagel Condensation Reaction in Microreactors Using a New Zeolite Catalyst" Applied Catalysis vol. 261 pp. 109-118 (2004).
P. Gantenbein "Adsorption Speed and Mass Transfer Zone Analysis of Water Vapour on the Solid Sorbent Material Zeolite and Silicagel with the Focus on the Heat Exchanger Design" Schweizerisches Status-Seminar—Energie-und Umweltforschung im Bauwesen pp. 241-248 (2006).
Parex—UOP Technical Data Sheet (2006).
Minceva et al. "UOP's Parex: Modeling, Stimulation and Optimization" 2nd Mercosur Congress on Chemical Engineering; 4th Mercosur Congress on Process Systems Engineering.
Wang et al. "Fabrication of Zeolite Coatings on Stainless Steel Grids" Journal of Materials Science Letters, No. 20, pp. 2091-2094 (2001).
International Search Report and Written Opinion dated Mar. 11, 2010; International Application No. PCT/US2009/047359, International filing date Jun. 15, 2009.
International Search Report and Written Opinion dated Mar. 25, 2010; International Application No. PCT/US2009/046055, International filing date Jun. 3, 2009.
USPTO Office Action dated Mar. 5, 2010, U.S. Appl. No. 12/165,390, filed Jun. 30, 2008.
Response to Office Action dated Jun. 7, 2010, U.S. Appl. No. 12/165,390, filed Jun. 30, 2008.
USPTO Office Action dated Mar. 9, 2010, U.S. Appl. No. 12/165,359, filed Sep. 22, 2008.
Response to Office Action dated Jun. 7, 2010, U.S. Appl. No. 12/165,359, filed Sep. 22, 2008.
USPTO Office Action dated Mar. 9, 2010, U.S. Appl. No. 12/165,329, filed Jun. 30, 2008.
Response to Office Action dated Jun. 7, 2010, U.S. Appl. No. 12/165,329, filed Jun. 30, 2008.

* cited by examiner

*Primary Examiner* — Tam M Nguyen
(74) *Attorney, Agent, or Firm* — Mark R Willis

(57) ABSTRACT

Adsorbents and methods for the adsorptive separation of para-xylene from a mixture containing at least one other $C_8$ aromatic hydrocarbon (e.g., a mixture of ortho-xylene, meta-xylene, para-xylene, and ethylbenzene) are described. Suitable adsorbents comprise zeolite X having an average crystallite size of less than 1.8 microns. The adsorbents provide improved mass transfer, which is especially advantageous for improving productivity in low temperature, low cycle time adsorptive separation operations in a simulated moving bed mode.

15 Claims, 5 Drawing Sheets

ADSORBENTS WITH IMPROVED MASS TRANSFER PROPERTIES AND THEIR USE IN THE ADSORPTIVE SEPARATION OF PARA-XYLENE

FIELD OF THE INVENTION

The present invention relates to adsorbents and methods for the adsorptive separation of para-xylene from a mixture containing at least one other $C_8$ alkylaromatic hydrocarbon (e.g., a mixture of ortho-xylene, meta-xylene, para-xylene, and ethylbenzene). The adsorbents have improved mass transfer properties, which benefit the adsorptive separation process.

DESCRIPTION OF RELATED ART $C_8$ alkylaromatic hydrocarbons are generally considered to be valuable products, with a high demand for para-xylene. In particular, the oxidation of para-xylene is used to commercially synthesize terephthalic acid, a raw material in the manufacture of polyester fabrics. Major sources of para-xylene include mixed xylene streams that result from the refining of crude oil. Examples of such streams are those resulting from commercial xylene isomerization processes or from the separation of $C_8$ alkylaromatic hydrocarbon fractions derived from a catalytic reformate by liquid-liquid extraction and fractional distillation. The para-xylene may be separated from a para-xylene-containing feed stream, usually containing a mixture of all three xylene isomers, by crystallization and/or adsorptive separation. The latter technique has captured the great majority of the market share of newly constructed plants for the production of para-xylene.

Accordingly, numerous patents are directed to the adsorptive separation of para-xylene from feed streams containing a mixture of $C_8$ alkylaromatics. Zeolites X and Y have been used to selectively adsorb para-xylene. See, for example, U.S. Pat. Nos. 3,686,342, 3,903,187, 4,313,015, 4,899,017, 5,171,922, 5,177,295, 5,495,061, and 5,948,950. U.S. Pat. No. 4,940,830 describes a rejective separation of para-xylene from other xylene isomers and ethylbenzene using sodium zeolite Y or a sodium zeolite Y that is also ion-exchanged with a Groups IB or Group VII element. A gas-phase process using adsorptive separation to recover para-xylene from a mixture of xylenes, with an adsorbent comprising a crystalline molecular sieve having an average crystal size between 0.5 and 20 microns is described in WO 2008/033200.

There remains a need in the art for improved adsorbents and processes for the efficient separation of para-xylene from a relatively impure mixture of $C_8$ alkylaromatic hydrocarbons.

SUMMARY OF THE INVENTION

The invention relates to adsorbents that selectively adsorb para-xylene over at least one other $C_8$ alkylaromatic compound present in a mixture. Due to the practical limitations of reaction equilibrium/selectivity, as well as evaporative (distillation) separations, typical mixtures obtained from oil refining processes contain the other xylene isomers, ortho-xylene and meta-xylene (in addition to para-xylene), in varying amounts and usually also contain ethylbenzene. Such mixtures will normally constitute feed streams used in methods associated with the invention.

Accordingly, embodiments of the invention are directed to processes for separating para-xylene from a relatively impure mixture of one or more $C_8$ alkylaromatic hydrocarbons other than the desired para-xylene. The mixture is contacted under adsorption conditions with an adsorbent comprising zeolite X. Aspects of the invention are associated with the finding that "small-crystallite-size zeolite X" (i.e., zeolite X having an average crystallite size below 1.8 microns, and typically from about 500 nanometers to about 1.5 microns) provides highly favorable performance when incorporated into adsorbents used in the adsorptive separation of para-xylene. In particular, the mass transfer rate of (i) para-xylene into the zeolite pores during adsorption and (ii) desorbent into the zeolite pores to displace adsorbed para-xylene during desorption, are significantly greater, relative to zeolite X synthesized according to conventional methods (and typically having an average crystallite size of 1.8 microns or more).

This increase in mass transfer rate is especially advantageous in the case of low temperature operation (less than about 175° C.), where mass transfer limitations associated with zeolite X-containing adsorbents, having conventional zeolite X crystallite sizes, are more commercially significant. Low temperature operation is desirable for a number of reasons, including increased para-xylene adsorptive selectivity and adsorbent capacity, as well as increased liquid feed density, all of which directionally improve para-xylene productivity. Yet in a simulated moving bed mode of operation, which is often used in continuous industrial processes for the adsorptive separation of para-xylene from a feed mixture of ortho-xylene, meta-xylene, para-xylene, and ethylbenzene, these advantages associated with lower operating temperatures have been found to diminish as cycle time decreases, due to mass transfer limitations associated with para-xylene adsorption/desorption. Adsorbents having improved mass transfer properties can therefore exploit the improvements in para-xylene capacity and selectivity, as discussed above, associated with lower temperature operation. Increased para-xylene productivity and consequently improved process economics, are made possible.

Aspects of the invention relate to adsorbents comprising small-crystallite-size zeolite X, as discussed above, which is bound with a binder such as clay, alumina, silica, zirconia, or mixtures of these materials. In a representative embodiment, such a binder is present in an amount from about 10% to about 40% by weight, relative to the total adsorbent weight.

The adsorbents comprising small-crystallite-size zeolite X may be used in solid adsorbents employed in fixed bed, moving bed, or simulated moving bed adsorptive separation processes employing conventional adsorption conditions. Adsorption may be performed in the liquid or gas phase, with liquid phase adsorption conditions normally being favored. When employed for the adsorptive separation of para-xylene in a simulated moving bed mode, the high mass transfer properties of the adsorbents described above allow for relatively increased para-xylene productivity, especially at in the case of low cycle time operation, in comparison to conventional adsorbents operating at the same overall percentage of para-xylene recovery. That is, the adsorbent bed concentration profiles are not adversely affected when cycle time is, for example, less than about 34 minutes (e.g., in the range from about 24 minutes to about 34 minutes). The cycle time of a simulated moving bed adsorptive separation process refers to the time for any of the inlet or outlet streams to return to its original adsorbent bed position. Therefore, in a typical simulated moving bed mode of operation with 24 adsorbent beds (e.g., two vessels each having 12 beds), the cycle time refers, for example, to the time required for the inlet feed stream, initially introduced into the first bed at time zero, to again be introduced to this bed. All other factors (e.g., para-xylene purity and recovery) being equal, shorter cycle times translate to higher productivity.

Particular embodiments of the invention thus relate to a process for separating para-xylene from a mixture comprising at least one other $C_8$ alkylaromatic hydrocarbon, with the mixture normally containing the xylene isomers ortho- and meta-xylene as well as ethylbenzene. The process comprises contacting the mixture with an adsorbent comprising small-crystallite-size zeolite X having average zeolite crystallite sizes in the ranges as discussed above. Exemplary adsorption temperatures range from about 60° C. (140° F.) to about 250° C. (480° F.). However, by virtue of their improved mass transfer properties, operation at lower temperatures with these adsorbents does not impose the appreciable mass transfer limitations associated with conventional adsorbents. Therefore, as explained above, the benefits associated with improved adsorptive para-xylene selectivity and adsorbent capacity at relatively low temperatures can be more fully realized. Adsorption temperatures of less than about 175° C. (350° F.), for example from about 150° C. (300° F.) to about 175° C. (350° F.), are particularly advantageous when used with the adsorbents described above. Adsorption pressures may range from slightly above atmospheric pressure, for example about 1 barg (15 psig) to about 40 barg (580 psig).

The small-crystallite-size zeolite X used to formulate adsorbents for such adsorptive separations will generally have a molecular silica to alumina ($SiO_2/Al_2O_3$) molar ratio from about 2.0 to about 4.0, corresponding to an atomic Si/Al ratio from about 1.0 to about 2.0. The zeolite normally has at least 95%, and typically substantially all (at least 99%), of its ion-exchangeable sites exchanged with barium or a combination of barium and potassium. For example, a representative adsorbent comprises small-crystallite-size zeolite X having from about 60% to about 100% of its ion-exchangeable sites exchanged with barium and from about 0% to about 40% of its ion-exchangeable sites exchanged with potassium.

The contact between the mixture of $C_8$ alkylaromatic hydrocarbons described above (e.g., as a continuous or batch process feed stream) effects or brings about the adsorption of para-xylene into the zeolite X pores, in preference to at least one other $C_8$ alkylaromatic hydrocarbon and normally in preference to all of such hydrocarbons present in the mixture. Therefore, an adsorbed phase (i.e., within the small-crystallite-size zeolite X pores) will be selectively enriched in para-xylene content, relative to that of the mixture of $C_8$ alkylaromatic compounds (e.g., the feed stream). If the mixture contains ortho-xylene, meta-xylene, para-xylene, and ethylbenzene, then para-xylene will be present in the adsorbed phase, in an enriched amount relative to the mixture, and ortho-xylene, meta-xylene, and ethylbenzene will be present in the non-adsorbed phase, in enriched amounts relative to the mixture.

The non-adsorbed phase may then be removed from (or flushed) from contact with the adsorbent, for example in a raffinate stream. The adsorbed phase, enriched in para-xylene, may be separately desorbed from the adsorbent, for example in an extract stream. A desorbent stream comprising a desorbent, for example an aromatic ring-containing compound such as toluene, benzene, indan, para-diethylbenzene, 1,4-diisopropylbenzene, or a mixture thereof may be used for both the flushing and desorption. An exemplary adsorptive separation process utilizing adsorbents discussed above may be performed continuously in a simulated moving bed mode. According to this embodiment, a $C_8$ alkylaromatic hydrocarbon feed stream as described above and the desorbent stream are charged into a fixed bed of the adsorbent, while the extract and raffinate streams are removed from the bed. The charging and removal of these streams may be performed continuously.

During a simulated moving bed mode or other type of adsorptive separation mode, it may be desired to monitor the water content of an outlet stream, such as an extract or raffinate stream, in order to determine the water content or level of hydration of the adsorbent. If necessary, water may be added to an inlet stream, such as a feed stream and/or desorbent stream, either continuously or intermittently, to maintain a desired level of adsorbent hydration (e.g., corresponding to a Loss in Ignition from about 5% to about 7%). Alternatively, water may be added to obtain an absolute water content in the extract stream or raffinate stream, for example, from about 20 ppm by weight to about 120 ppm by weight, corresponding to this adsorbent hydration level or another desired adsorbent hydration level.

These and other aspects and features relating to the present invention are apparent from the following Detailed Description.

DETAILED DESCRIPTION

Figure 1:
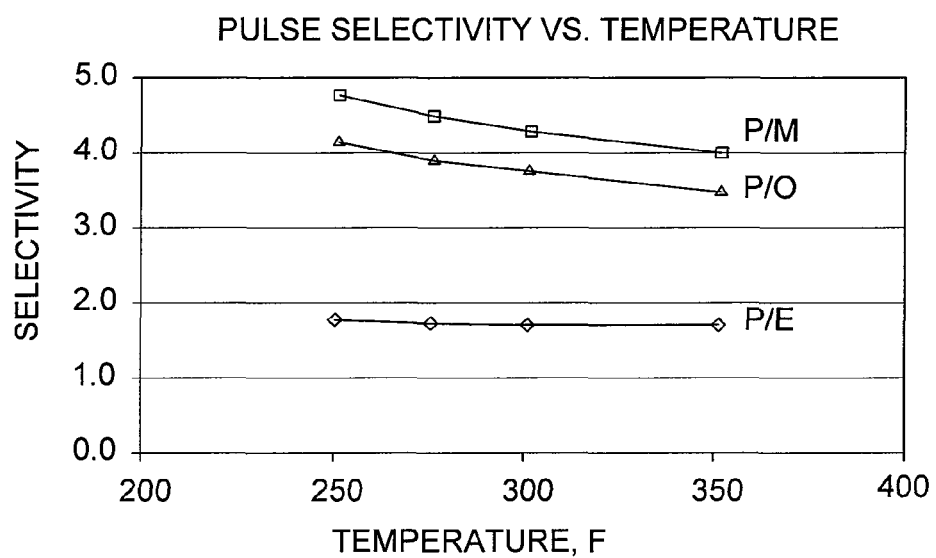
FIG. 1 shows the selectivities of feed mixture components (i.e., the para-xylene/meta-xylene selectivity, "P/M"; the para-xylene/ortho-xylene selectivity, "P/O"; and the para-xylene/ethylbenzene selectivity, "P/E"), as a function of temperature, obtained from a pulse test using an adsorbent comprising zeolite X.

As discussed above, the invention relates to the separation of para-xylene from a mixture comprising at least one other $C_8$ alkylaromatic hydrocarbon. The term separation refers to the recovery of para-xylene in a stream (e.g., a product stream) or fraction having an enriched para-xylene content (i.e., a content that is higher than initially present in the mixture). The separation is achieved through contacting the mixture with an adsorbent comprising zeolite X having an average crystallite size of less than 1.8 microns, and typically in the range from about 500 nanometers to about 1.5 microns.

Zeolite X is described in detail in U.S. Pat. No. 2,882,244. Small-crystallite-size zeolite X can be prepared from a seeded synthesis, where a seed or initiator material, used as a means of nucleation or starting zeolite crystallite growth, is first prepared and then blended into a gel composition at a gel composition:seed ratio corresponding to a targeted crystallite size. The ratio of gel composition to seed governs the relative number or concentration of nucleation sites, which in turn affects the crystallite size of the zeolite X that is synthesized. Higher amounts or concentrations of seed directionally reduce the crystallite size. For example, zeolite X preparations having average crystallite sizes of 2 microns and 0.5 microns can be made using gel:seed ratios of about 5400:1 and 85:1, by weight, respectively. In view of the present disclosure, those having skill in the art can readily vary the weight ratios to achieve other average crystallite sizes. A typical gel composition comprises $Na_2O$, $SiO_2$, $Al_2O_3$, and water. For each mole of $Al_2O_3$, about 1-5 moles of $Na_2O$ and $SiO_2$, and about 100-500 moles of water, can be used in the gel.

The gel composition may be prepared by combining a gel makeup solution with an aluminate makeup solution containing, for example, about 12% alumina by weight. The gel makeup solution is prepared by mixing water, caustic solution, and sodium silicate, and cooling the mixture to about 38° C. (100° F.). The aluminate makeup solution is prepared by dissolving alumina trihydrate in a caustic solution, with heating as necessary for dissolution, followed by cooling and aging at about 38° C. (100° F.) prior to combining it with the gel makeup solution. The gel makeup solution and aluminate solution are then combined under vigorous agitation for a short period (e.g., about 30 minutes), prior to adding the required amount of seed.

The seed is prepared in a similar manner to the gel composition. A typical seed composition therefore also comprises $Na_2O$, $SiO_2$, $Al_2O_3$, and water. For each mole of $Al_2O_3$, about 10-20 moles of $Na_2O$ and $SiO_2$, and about 150-500 moles of water, can be used. The aluminate solution used in preparing the seed may contain, for example, about 18% alumina by weight. After the gel composition and seed are combined, the mixture is heated while agitation is maintained, and then aged under agitated conditions for a time from about 5 to about 50 hours and at a temperature from about 25° C. (75° F.) to about 150° C. (300° F.) to achieve the desired crystallite formation from the seed nuclei. The resulting solid material may then by filtered, washed, and dried to obtain the prepared, small-crystallite-size zeolite X.

Typically, the crystallites of the small-particle-size zeolite X are bound with a suitable binder (e.g., an amorphous inorganic matrix such as clay, alumina, silica, zirconia, or mixtures thereof) into considerably larger adsorbent particles (e.g., in the range of about 16-60 Standard U.S. Mesh size) for use adsorptive separations. The process involves combining the small-particle-size zeolite X with water and binder to provide agglomerates, in the form of beads, extruded pellets, or other forms that may be prepared by conventional methods such as those described in U.S. Pat. No. 4,818,508. The agglomerates are subjected to firing at a temperature of about 500-700° C. to convert the green agglomerates into stronger particles.

Clays, including those comprising both silica and alumina, are exemplary materials for the non-zeolitic, amorphous binder of the adsorbent, which is present in intimate mixture with the zeolite crystallites. Specific types of clays are attapulgite, minugel, and kaolin. The binder or matrix material may be an adjunct of the manufacturing process for the zeolite (e.g., from the intentionally incomplete purification of the zeolite during its manufacture) or it may be added to the relatively pure zeolite. In either case its usual function of the binder is to aid in forming the small-size zeolite X crystallites into hard adsorbent particles, such as extrudates, aggregates, tablets, macrospheres or granules having a desired particle size range.

The zeolite will ordinarily be present in the adsorbent particles in an amount from about 75% to about 95% based on the volatile-free weight of the adsorbent composition. Volatile-free compositions are obtained by calcining the adsorbent, for example, at 900° C.

Normally, the small-crystallite-size zeolite X that is incorporated into the adsorbent particles is prepared in sodium form and the sodium cations may be partially or wholly exchanged by different cations, such as barium, potassium, strontium, and/or calcium, using known techniques. For example, small-crystallite-size zeolite X synthesized with at least some of its ion-exchangeable sites in sodium ion form may be immersed in a barium ion containing solution, or a barium and potassium ion containing solution, at conditions of time and temperature (e.g., about 0.5 to about 10 hours at about 20 to about 125° C.) which can effect ion exchange or replacement of sodium ions with barium and/or potassium ions. Filtration of the zeolite, removal from the solution, and re-immersion in a fresh solution (e.g., having the same or different ratios or cations or other types of cations) can be repeated until a desired level of exchange, with the desired types and ratios of cations, is achieved. Ion-exchange can also be conducted in a column operation according to known techniques, for example by pumping preheated barium chloride/potassium chloride solutions through a column of the adsorbent particles to completely displace the sodium cations of the small-crystallite-size zeolite X. Normally, the small-crystallite-size zeolite X used in adsorbents described herein have at least 95% or substantially all (e.g., at least 99%) of their ion-exchangeable sites exchanged with barium or a combination of barium and potassium. Generally, no other metal ions occupy ion-exchangeable sites in an amount effective to alter the adsorptive properties of the zeolite. In a representative embodiment, small-crystallite-size zeolite X will have from about 60% to about 100% of its ion-exchangeable sites exchanged with barium and from about 0% to about 40% of its ion-exchangeable sites exchanged with potassium.

The number of ion-exchangeable sites decreases as the zeolite $SiO_2/Al_2O_3$ molar ratio increases. Also, the total number of cations per unit cell decreases as monovalent cations (e.g., $K^+$) are replaced by divalent cations (e.g., $Ba^{+2}$). Within the zeolite X crystal structure, there exist many ion-exchangeable site locations, some of these being in positions outside of the supercages. Overall, the number and locations of cations in the zeolite crystal structure will depend upon the sizes and numbers of the cations present, as well as the $SiO_2/Al_2O_3$ molar ratio of the zeolite.

Those skilled in the art will recognize that the performance of an adsorbent (e.g., in terms of para-xylene purity and recovery into an extract stream) is influenced by a number of process variables, including operating conditions, feed stream composition, water content, and desorbent type and composition. The optimum adsorbent composition is therefore dependent upon a number of interrelated variables. In general, processes for the adsorptive separation of para-xylene from a mixture containing at least one other $C_8$ alkylaromatic hydrocarbon, as described herein, can achieve high para-xylene purity (e.g., at least about 99 wt-% or even at least about 99.5 wt-%) in the extract product stream with a high overall recovery of para-xylene from the feed stream (e.g., at least about 90%, from about 92% to about 99.5%, or from about 95% to about 99%).

One consideration associated with overall adsorbent performance is its water content, which may be determined from a Loss on Ignition (LOI) test that measures the weight difference obtained by drying a sample of the unused adsorbent at 900° C. under an inert gas purge such as nitrogen for a period of time (e.g., 2 hours) sufficient to achieve a constant weight. The sample is first conditioned at 350° C. for 2 hours. The percentage of weight loss, based on the initial sample weight, is the LOI at 900° C. An LOI from about 4% to about 7%, and preferably from about 4% to about 6.5%, by weight is generally desired for the adsorbents comprising small-crystallite-size zeolite X. An increased LOI value may be achieved by equilibrating a fixed amount of adsorbent, having a lower LOI than desired, and a fixed amount of water in a sealed dessicator until equilibrium is established. The LOI value of an adsorbent may be decreased through drying at 200-350° C. under an inert gas purge or vacuum for a period of time (e.g., 2 hours).

To monitor the adsorbent LOI during an adsorptive separation process, it may be desired to determine the water content of a suitable outlet stream of such a process, for example the raffinate stream and/or extract stream. Also, the adsorbent LOI may be adjusted or maintained, if desired, through continuous or intermittent addition or injection of water into a suitable inlet stream, for example the feed stream or desorbent stream. According to one exemplary embodiment, the adsorbent LOI is maintained by monitoring the water content in the extract and/or raffinate streams. For example, a representative range of water in either or both of these streams, corresponding to a desirable adsorbent LOI, is from about 20 ppm by weight to about 120 ppm by weight. Often the desired water content in one or both of these outlet streams is from about 40 ppm to about 80 ppm by weight. Water may be added to either the feed stream or the desorbent stream, as discussed above, in continuous or intermittent injections to maintain these measured water levels in the extract stream, raffinate stream, or both.

It is recognized that LOI is an indirect or relative measurement of the adsorbent hydration level (or water content), as other volatile components (e.g., organic materials) are also lost during the analysis. Therefore, the desired adsorbent water content is simply that which corresponds to an LOI from about 4% to about 7% by weight, measured as described above. If necessary, the absolute amount of water in a zeolitic adsorbent sample can be determined by known analytical methods such as Karl Fischer (ASTM D1364).

Although the adsorptive separation of para-xylene from other $C_8$ alkylaromatic compounds may be conducted in either the liquid phase or the vapor phase, predominantly liquid-phase operation is normally used. As discussed above, adsorption temperatures of less than about 175° C. (350° F.), for example from about 150° C. (300° F.) to about 175° C. (350° F.), are particularly advantageous when used with the adsorbents comprising small-crystallite-size zeolite X, as mass transfer limitations, which prevent conventional adsorbents from exploiting the improved para-xylene adsorptive selectivity and adsorbent capacity at these temperatures, are overcome. Adsorption conditions can also include a pressure in the range from about atmospheric pressure to about 600 psig, with pressures from about 1 barg (15 psig) to about 40 barg (580 psig) being typical. Desorption conditions often include substantially the same temperature and pressure as used for adsorption.

Separation of para-xylene is carried out by contacting a mixture of para-xylene and at least one other $C_8$ alkylaromatic hydrocarbon with an adsorbent, and under adsorption conditions, as described above. For example, a feed stream comprising the mixture of $C_8$ alkylaromatic hydrocarbons may be contacted with a bed of the adsorbent in order to selectively adsorb, in an adsorbed phase, the para-xylene, in preference to ortho-xylene, meta-xylene, and ethylbenzene. These other $C_8$ alkylaromatic components of the feed stream may selectively pass through the adsorption zone as a non-adsorbed phase.

Feed streams comprising mixtures of $C_8$ alkylaromatic hydrocarbons can be separated from various refinery process streams (e.g., reformate) including the products of separation units. Such separations are imprecise and the feed is therefore expected to contain limited amounts (e.g., less than 5 mol-%, and often less than 2 mol-%) of other compounds, such as $C_9$ alkylaromatic hydrocarbons. In most instances, the feed will be primarily $C_8$ alkylaromatic hydrocarbons and contain a total of less than 10 mol-%, typically less than 5 mol-%, and in some cases less than 1 mol-%, of other types of compounds. In one type of separation process, after the adsorptive capacity of the adsorbent is reached, the feed stream inlet flow to the adsorbent is stopped, and the adsorption zone is then flushed to remove a non-adsorbed phase, initially surrounding the adsorbent, from contact with the adsorbent. The adsorbed phase, enriched in the desired para-xylene, may be thereafter desorbed from the adsorbent pores by treating the adsorbent with a desorbent, normally comprising a cyclic hydrocarbon (e.g., an aromatic ring-containing hydrocarbon) such as toluene, benzene, indan, para-diethylbenzene, 1,4-diisopropylbenzene, or mixtures thereof. The same desorbent is commonly used for both (i) flushing the non-adsorbed phase into a raffinate stream comprising the desorbent and (ii) desorbing the adsorbed phase into an extract stream, also comprising the desorbent. Because the extract stream contains the adsorbed phase, which is enriched in para-xylene, the extract stream will also be enriched in para-xylene, relative to the feed stream, when considered on a desorbent-free basis.

As used herein, a "feed stream" is a mixture containing the desired extract component (para-xylene) and one or more raffinate components to be separated by the adsorptive separation process. A "feed mixture" (i.e., comprising "feed mixture components") therefore comprises the mixture of extract and raffinate components, such as a mixture of xylenes (ortho-xylene, meta-xylene, and para-xylene as discussed above) and ethylbenzene. The feed stream is an inlet stream to the adsorbent (e.g., in the form of one or more adsorbent beds) used in the process. An "extract component" is a compound or class of compounds that is selectively adsorbed by the adsorbent. A "raffinate component" is a compound or class of compounds that is less selectively adsorbed (or selectively rejected). A "desorbent" is generally any material capable of desorbing an extract component from the adsorbent, and a "desorbent stream" is an inlet stream to the adsorbent, which contains desorbent. A "raffinate stream" is an outlet stream from the adsorbent, in which a raffinate component is removed. The composition of the raffinate stream can vary from essentially 100% desorbent to essentially 100% raffinate components, with minor amounts one or more extract components. An "extract stream" is an outlet stream from the adsorbent, in which an extract component is removed. The composition of the extract stream can vary from essentially 100% desorbent to essentially 100% extract components, with minor amounts of one or more raffinate components.

Typically, at least some portion of the extract stream and the raffinate stream are purified (e.g., by distillation) to remove desorbent and thereby produce an extract product stream and a raffinate product stream. The "extract product stream" and "raffinate product stream" refer to products produced by the adsorptive separation process containing, respectively, an extract component and a raffinate component in higher concentration than present in the extract stream and the raffinate stream, respectively, and also in higher concentration than present in the feed stream.

The capacity of the adsorbent for adsorbing a specific volume of an extract component is an important characteristic, as increased capacity makes it possible to reduce the amount of adsorbent (and consequently the cost) needed to separate the extract component for a particular charge rate of feed mixture. Good initial capacity for the extract component, as well as total adsorbent capacity, should be maintained during actual use in an adsorptive separation process over some economically desirable life.

The rate of exchange of an extract component (para-xylene) with the desorbent can generally be characterized by the width of the peak envelopes at half intensity obtained from plotting the composition of various species in the adsorption zone effluent obtained during a pulse test versus time. The narrower the peak width, the faster the desorption rate. The desorption rate can also be characterized by the distance between the center of the tracer peak envelope and the disappearance of an extract component which has just been desorbed. This distance is time dependent and thus a measure of the volume of desorbent used during this time interval. The tracer is normally a relatively non-adsorbed compound which moves through an adsorbent column faster than the materials to be separated.

Selectivity ($\beta$), for an extract component with respect to a raffinate component may be characterized by the ratio of the distance between the center of the extract component peak envelope and the tracer peak envelope (or other reference point) to the corresponding distance between the center of the raffinate component peak envelope and the tracer peak envelope (or other reference point). The selectivity corresponds to the ratio of the two components in the adsorbed phase divided by the ratio of the same two components in the non-adsorbed phase at equilibrium conditions. Selectivity may therefore be calculated from:

$$\text{Selectivity} = (\text{wt-\%}\ C_A/\text{wt-\%}\ D_A)/(\text{wt-\%}\ C_U/\text{wt-\%}\ D_U)$$

where C and D are two components of the feed mixture represented in weight percent and the subscripts A and U represent the adsorbed and non-adsorbed phases, respectively. The equilibrium conditions are determined when the feed passing over a bed of adsorbent does not change composition, in other words, when there is no net transfer of material occurring between the non-adsorbed and adsorbed phases. In the equation above, a selectivity larger than 1.0 indicates preferential adsorption of component C within the adsorbent. Conversely, a selectivity less than 1.0 would indicate that component D is preferentially adsorbed leaving an non-adsorbed phase richer in component C and an adsorbed phase richer in component D.

For a selectivity of two components approaching 1.0, there is no preferential adsorption of one component by the adsorbent with respect to the other (i.e., they are both adsorbed to about the same degree with respect to each other). As selectivity deviates from 1.0, there is an increasingly preferential adsorption by the adsorbent for one component with respect to the other. Selectivity can be expressed not only for one feed stream compound relative to another (e.g., para-xylene to meta-xylene selectivity) but can also be expressed between any feed stream compound and the desorbent (e.g., para-xylene to para-diethylbenzene selectivity).

While separation of an extract component from a raffinate component is theoretically possible when the adsorbent selectivity for the extract component with respect to the raffinate component is only slightly greater than 1, it is preferred that this selectivity is at least 2 for process economic considerations. Analogous to relative volatility in fractional distillation, the higher the selectivity, the easier the adsorptive separation is to perform. Higher selectivities directionally permit a smaller amount of adsorbent to be used, just as higher relative volatilities require fewer theoretical stages of distillation (and a smaller column) to carry out a given distillation separation for a given feed.

The desorbent for an adsorptive separation process must be judiciously selected to satisfy several criteria. The desorbent should ideally displace an extract component from the adsorbent at a reasonable mass flow rate, without itself being so strongly adsorbed as to prevent an extract component from displacing the desorbent in a following adsorption cycle. In terms of the selectivity, it is preferred that the adsorbent be more selective for the extract component with respect to a raffinate component than it is for the desorbent with respect to the raffinate component. Additionally, the desorbent must be compatible with both the adsorbent as well as the feed mixture. In particular, the desorbent should not adversely effect the desired selectivity of the adsorbent for an extract component with respect to a raffinate component. Additionally, the desorbent should be essentially chemically inert with respect to extract and raffinate components, as both the extract stream and the raffinate stream are typically removed from the adsorbent in admixture with desorbent. Any chemical reaction involving desorbent and an extract component or a raffinate component would complicate or possibly prevent product recovery.

A performance parameter to be considered for the desorbent is therefore its rate of exchange for the extract component of the feed or, in other words, the relative rate of desorption of the extract component. This parameter relates directly to the amount of desorbent that must be used in an adsorptive separation process to desorb the extract component from the adsorbent. Faster rates of exchange reduce the amount of desorbent needed and therefore reduce operating costs associated with larger desorbent-containing process streams, including the separation and recycle of desorbent from these streams. A desorbent selectivity of 1 or slightly lower with respect to an extract component helps ensure that all the extract component is desorbed with a reasonable flow rate of desorbent, and also that extract components can displace desorbent in a subsequent adsorption step. As a final consideration, the desorbent should generally be readily available at a favorable cost.

Moreover, since both the raffinate stream and the extract stream normally contain desorbent, the desorbent should also be easily separable from the mixture of extract and raffinate components introduced in the feed stream. Without a method of separating desorbent in the extract stream and the raffinate stream, the concentration of an extract component in the extract product and the concentration of a raffinate component in the raffinate product would not be commercially favorable, nor would the desorbent be available for reuse in the process. At least a portion of the desorbent is therefore normally recovered from the extract stream and the raffinate stream of an adsorptive separation process by distillation or evaporation, although other separation methods such as reverse osmosis could also be used alone or in combination with distillation or evaporation. In this regard, the desorbent is generally a "light" or "heavy" desorbent that is easily separable, as a distillation overhead or bottoms product, respectively, from the $C_8$ alkylaromatic hydrocarbons in the extract stream and raffinate stream of a para-xylene adsorptive separation process.

A "pulse test" may be employed to test adsorbents with a particular feed mixture and desorbent to measure such adsorbent properties as adsorptive capacity, selectivity, resolution, and exchange rate. A representative pulse test apparatus includes a tubular adsorbent chamber of approximately 70 cubic centimeters (cc) in volume and having inlet and outlet portions at opposite ends of the chamber. The chamber is equipped to allow operation at constant, predetermined temperature and pressure. Quantitative and qualitative analytical equipment such as refractometers, polarimeters and chromatographs can be attached to an outlet line of the chamber and used to detect quantitatively and/or determine qualitatively one or more components in the effluent stream leaving the adsorbent chamber. During a pulse test, the adsorbent is first filled to equilibrium with a particular desorbent by passing the desorbent through the adsorbent chamber. A small volume or pulse of the feed mixture, which may be diluted with desorbent, is injected by switching the desorbent flow to the feed sample loop at time zero. Desorbent flow is resumed, and the feed mixture components are eluted as in a liquid-solid chromatographic operation. The effluent can be analyzed on-stream or, alternatively, effluent samples can be collected periodically and analyzed separately (off-line) and traces of the envelopes of corresponding component peaks plotted in terms of component concentration versus quantity of effluent.

Information derived from the pulse test can be used to determine adsorbent void volume, retention volume for an extract component or a raffinate component, selectivity for one component with respect to the other, stage time, the resolution between the components, and the rate of desorption of an extract component by the desorbent. The retention volume of an extract component or a raffinate component may be determined from the distance between the center of the peak envelope of an extract component or a raffinate component and the peak envelope of a tracer component or some other known reference point. It is expressed in terms of the volume in cubic centimeters of desorbent pumped during the time interval corresponding to the distance between the peak envelopes.

Retention volumes for good candidate systems fall within a range set by extrapolation to commercial designs. A very small retention volume indicates there is little separation between the two components (i.e., one component is not adsorbed strongly enough). Large extract component retention volumes indicate it is difficult for the desorbent to remove the retained extract component.

Conventional apparatuses employed in static bed fluid-solid contacting may be used in adsorptive separation processes incorporating an adsorbent comprising small-crystallite-size zeolite X, as described above. The adsorbent may be employed in the form of a single fixed bed which is alternately contacted with the feed stream and desorbent stream. The adsorbent may therefore be used in a single static bed that is alternately subjected to adsorption and desorption steps in a non-continuous (e.g., batch) process. A swing bed mode of operation is also possible, in which multiple beds are periodically used for a given operation or step.

Alternatively, a set of two or more static beds may be employed with appropriate piping/valves to allow continual passage of the feed stream through any one of a number of adsorbent beds while the desorbent stream is passed through one or more of the other beds in the set. The flow of the feed stream and desorbent may be either upward or downward through the adsorbent.

A countercurrent moving bed mode of operation provides another potential mode of operation, in which a stationary concentration profile of the feed mixture components can be achieved, allowing for continuous operation with fixed points of feed stream and desorbent stream introduction, as well as extract stream and raffinate stream withdrawal. Countercurrent moving bed or simulated moving bed countercurrent flow systems have a much greater separation efficiency than fixed adsorbent systems and are therefore very often used for commercial-scale adsorptive separations. In a simulated moving bed process, the adsorption and desorption are carried out continuously in a simulated moving bed mode, allowing both continuous production (withdrawal) of an extract stream and a raffinate stream (both outlet streams), as well as the continual use (input) of a feed stream and a desorbent stream (both inlet streams).

The operating principles and step sequence of a simulated moving bed flow system are described in U.S. Pat. No. 2,985,589, 3,310,486, and 4,385,993, incorporated by reference herein for their teachings with respect to simulated moving bed flow systems. In such systems, it is the progressive movement of multiple access points along an adsorbent chamber that simulates the movement of adsorbent (opposite the liquid access point movement) contained in one or more chambers. Typically only four of the many (16 to 24 or more) access lines to the chamber(s) are active at any one time, for carrying the feed stream, the desorbent stream, the raffinate stream, and the extract stream. Coincident with this simulated movement (e.g., upward movement) of the solid adsorbent is the movement (e.g., downward movement) of fluid occupying the void volume of the packed bed of adsorbent. The circulation of this fluid (e.g., liquid) flow may be maintained using pump. As an active liquid access point moves through a cycle, that is, through each adsorbent bed contained in one or more chambers, the chamber circulation pump generally provides different flow rates. A programmed flow controller may be provided to set and regulate these flow rates.

The active access points effectively divide the adsorbent chamber into separate zones, each of which has a different function. Three separate operational zones are generally present for the process to take place, although, in some cases, an optional fourth operation zone is used. The zone numbers used in the following description of a simulated moving bed process correspond to those illustrated in U.S. Pat. No. 3,392,113 and 4,475,954, also incorporated by reference herein with respect to their teachings regarding simulated moving bed operation.

The adsorption zone (zone 1) is defined as the adsorbent located between the inlet feed stream and the outlet raffinate stream. In this zone, the feed mixture contacts the adsorbent, an extract component is adsorbed, and a raffinate stream is withdrawn. The general flow through zone 1 is from the feed stream which passes into the zone to the raffinate stream which passes out of the zone, and the flow in this zone is normally considered to be in a downstream direction when proceeding from the inlet feed stream to the outlet raffinate stream.

Immediately upstream, with respect to fluid flow in zone 1, is the purification zone (zone 2).

The purification zone is defined as the adsorbent between the outlet extract stream and the inlet feed stream. The basic operations in this zone are the displacement from the non-selective void volume of the adsorbent of any raffinate component carried into zone 2 and the desorption of any raffinate component adsorbed within the selective pore volume of the adsorbent or adsorbed on the surfaces of the adsorbent particles. Purification is achieved by passing a portion of the extract stream leaving zone 3 into zone 2 at its upstream boundary, the extract outlet stream, to effect the displacement of raffinate components. The flow in zone 2 is in a downstream direction from the extract outlet stream to the feed inlet stream. This material then joins the feed stream and flows through zone 1.

Immediately upstream of zone 2 with respect to the fluid flowing in zone 2 is the desorption zone (zone 3). The desorption zone is defined as the adsorbent between the inlet desorbent stream and the outlet extract stream. The function of the desorbent zone is to allow a desorbent which passes into this zone to displace the extract component which was adsorbed in the adsorbent during a previous contact with the feed mixture in zone 1, in a prior cycle of operation. The flow of fluid in zone 3 is essentially in the same direction as that in zones 1 and 2.

In some instances, an optional buffer zone (zone 4) may be utilized. This zone, defined as the adsorbent between the outlet raffinate stream and the inlet desorbent stream, if used, is located immediately upstream with respect to the fluid flow into zone 3. Zone 4 can be utilized to conserve the amount of desorbent needed for desorption, since a portion of the raffinate stream which is removed from zone 1 can be passed into zone 4 to displace desorbent from that zone out into the desorption zone. Zone 4 will contain enough adsorbent so that raffinate components in the raffinate stream passing from zone 1 into zone 4 can be prevented from passing into zone 3 and thereby contaminating the extract stream withdrawn from zone 3. If a fourth operational zone is not utilized, the raffinate stream passed from zone 1 to zone 4 must be carefully monitored in order that the flow directly from zone 1 to zone 3 can be stopped when there is an appreciable quantity of raffinate components present in the raffinate stream passing from zone 1 into zone 3 so that the extract outlet stream is not contaminated.

A cyclic advancement of the input (feed and desorbent) streams and output (extract and raffinate) streams through fixed beds of adsorbent, to provide a continuous process performed in a simulated moving bed mode, can be accomplished by utilizing a manifold system in which the valves in the manifold are operated in a manner which effects the shifting of the input and output streams thereby providing a flow of fluid with respect to solid adsorbent in a simulated countercurrent manner. Another type of operation which can simulate countercurrent flow of solid adsorbent involves the use of a rotating valve in which the input and output streams are each directed by the valve to one of the many lines connected to the adsorbent chamber and by which the location at which the input feed stream, output extract stream, input desorbent stream, and output raffinate stream enter or leave the chamber are advanced in the same direction along the adsorbent bed. Both the manifold arrangement and rotary disc valve are known in the art. A multiple valve apparatus is described in detail in U.S. Pat. No. 4,434,051. Rotary disc valves which can be utilized in this operation are described in U.S. Pat. Nos. 3,040,777, 4,632,149, 4,614,204, and 3,422,848. These patents disclose a rotary type valve in which the suitable advancement of the various input and output streams from fixed sources can be achieved without difficulty.

In many instances, one operational zone of a simulated moving bed process will contain a much larger quantity of adsorbent than another operational zone. For instance, in some operations the buffer zone can contain a minor amount of adsorbent compared to the adsorbent present in the adsorption and purification zones. As another example, in instances in which a desorbent is used that easily desorbs the extract component from the adsorbent, a relatively small amount of adsorbent will be needed in the desorption zone compared to the amount of adsorbent needed in the buffer zone, adsorption zone, purification zone or all of these zones. Also, it is not required that the adsorbent be located in a single chamber (i.e., column or vessel), and often two adsorbent chambers (e.g., each provided with 12 access lines) are used. Additional chambers are also contemplated.

Normally at least a portion of the output extract stream will pass to a separation process such as a fractionation column, in order to recover a portion of the desorbent (e.g., for recycle to the adsorptive separation process as a desorbent recycle stream) and produce a purified extract product stream (e.g., containing a reduced amount of desorbent). Preferably at least a portion of the output raffinate stream will also pass to a separation process, in order to recover another portion of the desorbent (e.g., also for recycle to the adsorptive separation process) and a raffinate product stream (e.g., also containing a reduced concentration of desorbent). In large-scale petrochemical units, essentially all of the desorbent is recovered for reuse. The design of fractional distillation facilities for this recovery will be dependent on the materials being separated, the desorbent composition, etc.

Another type of a simulated moving bed flow system suitable for use in adsorptive separation processes described above is a co-current high efficiency simulated moving bed process described in U.S. Pat. No. 4,402,832 and 4,478,721, incorporated by reference herein with respect to their teachings of this alternative mode of operation. This process has advantages in terms of energy efficiency and reduced capital costs, in cases where products of slightly lower purity are acceptable to the producer.

The scale of adsorptive separation units for the purification of para-xylene can vary from those of pilot plant scale (see, for example, U.S. Pat. No. 3,706,812) to commercial scale and can range in produce flow rates from as little as a few milliliters an hour to many hundreds of cubic meters per hour.

Overall, aspects of the invention are directed to the exploitation of the unique properties of small-crystallite-size zeolite X for use in adsorptive separations, and particularly in commercial simulated moving bed operations. In view of the present disclosure, it will be seen that several advantages may be achieved and other advantageous results may be obtained. Those having skill in the art, with the knowledge gained from the present disclosure, will recognize that various changes could be made in the above adsorbent compositions, and processes using these compositions, without departing from the scope of the present disclosure. The chemical processes, mechanisms, modes of interaction, etc. used to explain theoretical or observed phenomena or results, shall be interpreted as illustrative only and not limiting in any way the scope of the appended claims.

The following examples are set forth as representative of the present invention. These examples are not to be construed as limiting the scope of the invention as these and other equivalent embodiments will be apparent in view of the present disclosure and appended claims.

EXAMPLE 1

Selectivity Testing

A conventional adsorbent comprising zeolite X exchanged with barium and potassium, and having an LOI of 6 wt-%, was evaluated in the adsorptive separation of para-xylene. A standard pulse test as described above was performed by first loading the adsorbent in a 70 cc column under the desorbent para-diethylbenzene. A feed pulse containing equal quantities of ethylbenzene and each of the three xylene isomers, together with a normal nonane (n-$C_9$) tracer, was injected. Pulse tests were performed at various column temperatures in the range from 121° C. to 177° C. (250° F. to 350° F.) to examine the effect of temperature on selectivity. The para-xylene selectivities were determined from the component peaks obtained from each of these pulse tests, and the results are shown in FIG. 1.

The results show that the para-xylene/meta-xylene selectivity, "P/M," and the para-xylene/ortho-xylene selectivity, "P/O," increase at lower adsorption temperatures, while the para-xylene/ethylbenzene selectivity, "P/E," varies little with respect to temperature. This demonstrates that lower adsorptive separation temperatures are favored from a thermodynamic equilibrium (although not necessarily from a kinetic) standpoint.

EXAMPLE 2

Capacity Testing

Figure 2:
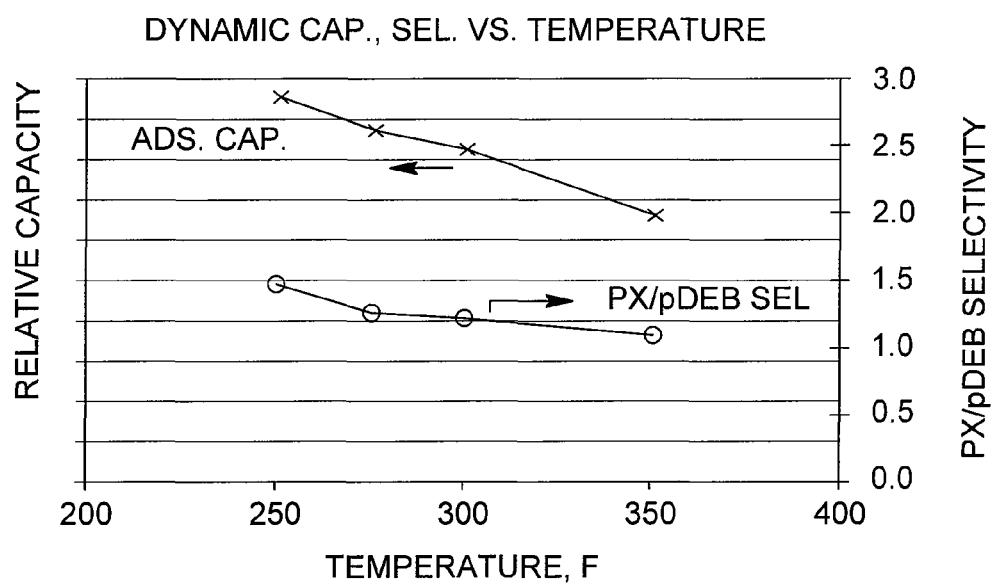
FIG. 2 shows the capacity of an adsorbent comprising zeolite X, as well as the para-xylene/para-diethylbenzene selectivity, "PX/pDEB Sel," as a function of temperature, obtained from a breakthrough (or dynamic) test.

A chromatographic separation (dynamic capacity or breakthrough test) was performed using a conventional adsorbent as described in Example 1. A column containing 70 cc of the adsorbent, initially loaded under para-diethylbenzene, was charged with a sample feed mixture containing ortho-xylene, meta-xylene, para-xylene, and ethylbenzene. Breakthrough tests were performed at various column temperature in the range from 121° C. to 177° C. (250° F. to 350° F.) to examine the effect of temperature on adsorbent capacity and para-xylene/para-diethylbenzene selectivity, "PX/pDEB Sel," and the results are shown in FIG. 2. The results further confirm that lower adsorptive separation temperatures are favorable, in terms of total adsorbent capacity, without adversely affecting the para-xylene/desorbent selectivity.

EXAMPLE 3

Mass Transfer Rate

Figure 3:
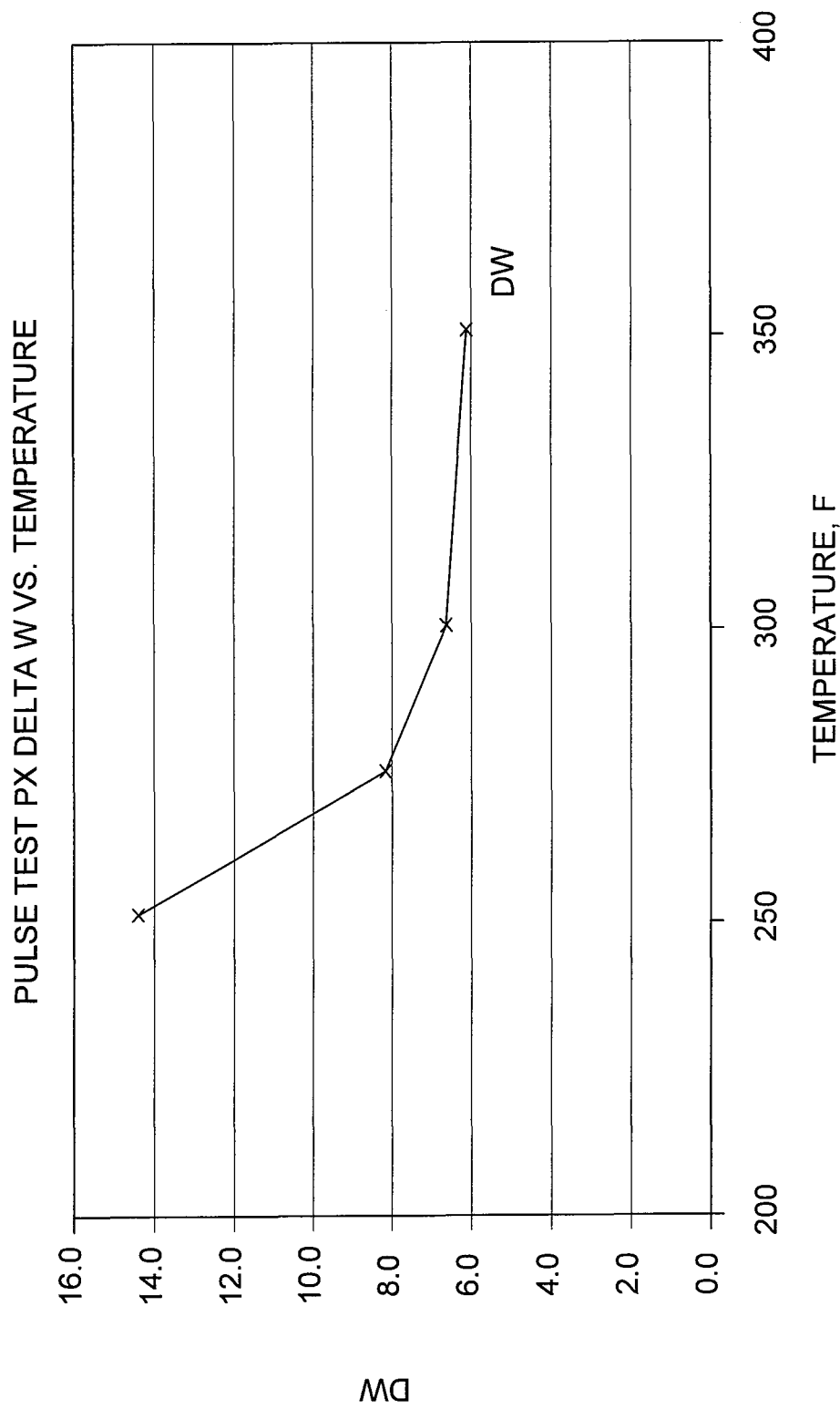
FIG. 3 shows the "DW" or "Delta W," namely the half width of the para-xylene peak (i.e., peak envelope width at half intensity), minus the half-peak width of normal nonane (n-$C_9$) tracer peak, as a function of temperature, obtained from a pulse test using an adsorbent comprising zeolite X.

Using the data obtained from pulse tests as described in Example 1, the "DW" or "Delta W," namely the half width of the para-xylene peak (i.e., peak envelope width at half intensity), minus the half width of normal nonane tracer peak (to account for dispersion), was determined as a function of temperature. The results are shown in FIG. 3 and indicate that mass transfer limitations become significant in conventional para-xylene adsorptive separation processes at temperatures below about 177° C. (350° F.).

EXAMPLE 4

Figure 4:
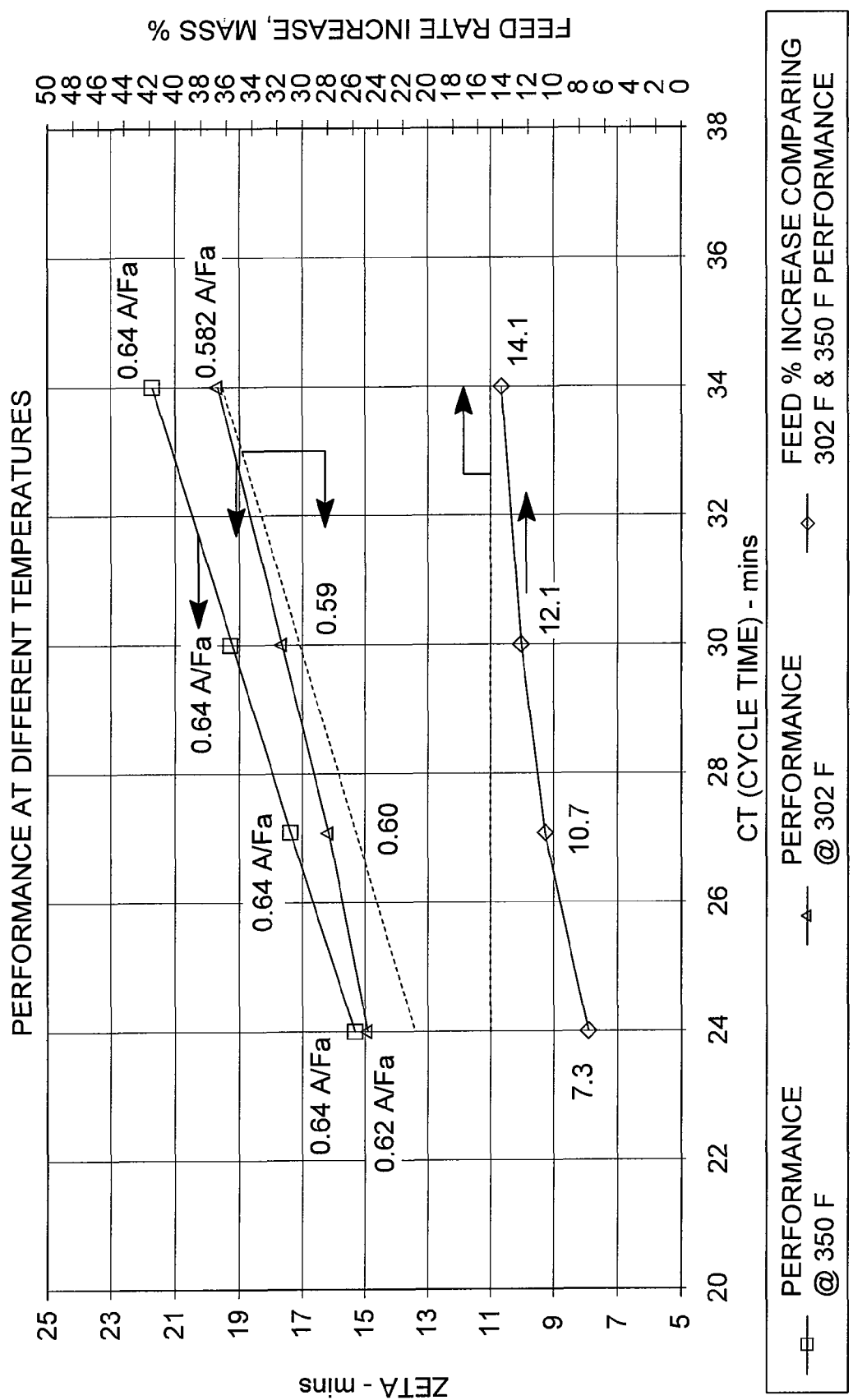
FIG. 4 shows the performance of a para-xylene adsorptive separation process operating in a simulated moving bed mode at temperatures of 150° C. (302° F.) and 177° C. (350° F.).

Adsorptive Separation of Para-Xylene in Simulated Moving Bed Mode, Temperature Effects The performance of a conventional adsorbent, as described in Example 1, in the adsorptive separation of para-xylene in a pilot plant operating in a simulated moving bed mode is illustrated in FIG. 4. At all conditions analyzed, the total para-xylene recovered in the extract stream was about 95 wt-%. Measured performance parameters at 150° C. (302° F.) are shown (solid square symbols), compared to those at 177° C. (350° F.) (solid triangular symbols), as a function of the process cycle time. In all cases, the value of zeta (Y-axis, left side) at the lower temperature was below the corresponding value at the higher temperature, indicating that higher para-xylene productivity was achieved at lower operating temperature, due to the improved para-xylene adsorption selectivity and adsorbent capacity, as confirmed in the pulse and breakthrough tests, described in Examples 1 and 2.

The zeta value is a measure of selective pore volume required for processing a unit volumetric rate of para-xylene containing feed. Lower zeta values therefore directionally indicate higher throughput or productivity. In particular, the zeta value is calculated as the product of $A/F_a$ and $\theta$, where A is the rate of simulated circulation of the selective adsorbent pore volume, $F_a$ is the volumetric rate of the feed stream containing the mixture of $C_8$ alkylaromatic hydrocarbons, and $\theta$ is the cycle time. The quantity $A/F_a$ is shown in FIG. 4 for each combination of cycle time and temperature tested. The near convergence, at low cycle times, of the curves generated at high and low temperature operation indicates that the low temperature performance advantages become less pronounced as cycle time is reduced (and as productivity or zeta is maximized).

This barrier to obtaining even higher productivity, observed in practice, is due to mass transfer limitations. The bottom curve in FIG. 4 (open diamonds) illustrates the impact of mass transfer limitations on productivity, in terms of the possible feed stream volumetric rate increase (Y-axis, right side) that is obtained by reducing operating temperature from 177° C. (350° F.) to 150° C. (302° F.) at each cycle time. For a cycle time of 34 minutes, for example, the benefit of lower operating temperature translates into an approximately 14% increase in the volumetric rate at which the $C_8$ alkylaromatic feed stream that can be processed. The productivity advantage, however, decreases to only about 7% for a cycle time of 24 minutes, as a result of mass transfer limitations. The dashed lines in FIG. 4, in contrast, illustrate the para-xylene adsorptive separation performance parameters and feed productivity advantages that are theoretically possible in the absence of mass transfer limitations.

The laboratory and pilot plant scale studies described in Examples 1-4 therefore illustrate that, while lower operation temperature results in significant advantages in adsorbent capacity, adsorption selectivity, and increased liquid density per unit volume of adsorbent, it also reduces the mass transfer rate. As a result, it is difficult to take full advantage of the thermodynamically favorable operating regime, at temperatures ranging from about 150° C. (300° F.) to about 175° C. (350° F.), in the adsorptive separation of para-xylene from a relatively impure mixture of $C_8$ alkylaromatic hydrocarbons. As is shown in FIG. 4, with decreasing cycle time, the productivity advantage of 150° C. (300° F.) operation decreases in the case of conventional adsorbents.

EXAMPLE 5

Adsorptive Separation of Para-Xylene in Simulated Moving Bed Mode, Bed Concentration Profiles The feed mixture component and desorbent concentration profiles for each of 24 adsorbent beds, obtained during the adsorptive separation of para-xylene in a pilot plant operating in a simulated moving bed mode using a conventional adsorbent (as described in Example 1) were evaluated. A liquid composition "survey" (i.e., analysis of the liquid composition in each bed) was performed during steady state operation at 150° C. (302° F.) and about 95% recovery of para-xylene in the extract stream. The concentration profiles were obtained using a cycle time of 34 minutes and 24 minutes, respectively. The survey results confirmed that significant mass transfer limitations prevent full realization of the more favorable para-xylene adsorption selectivity and adsorbent capacity at this temperature. The adverse effects of limited mass transfer were manifested in a more dispersed para-xylene front in the adsorption zone (zone I, as discussed above). The theoretical productivity increase associated with low temperature operation cannot be realized, using a conventional adsorbent, as cycle time is reduced to more commercially desirable values (e.g., 24-34 minutes).

High Resolution Scanning Electron Microscopy (HR SEM) micrographs of adsorbents comprising zeolite X (with differing amounts of binder) also illustrated that the zeolite X crystallites present the main diffusion path that limits the mass transfer rate.

EXAMPLE 6

Figure 5:
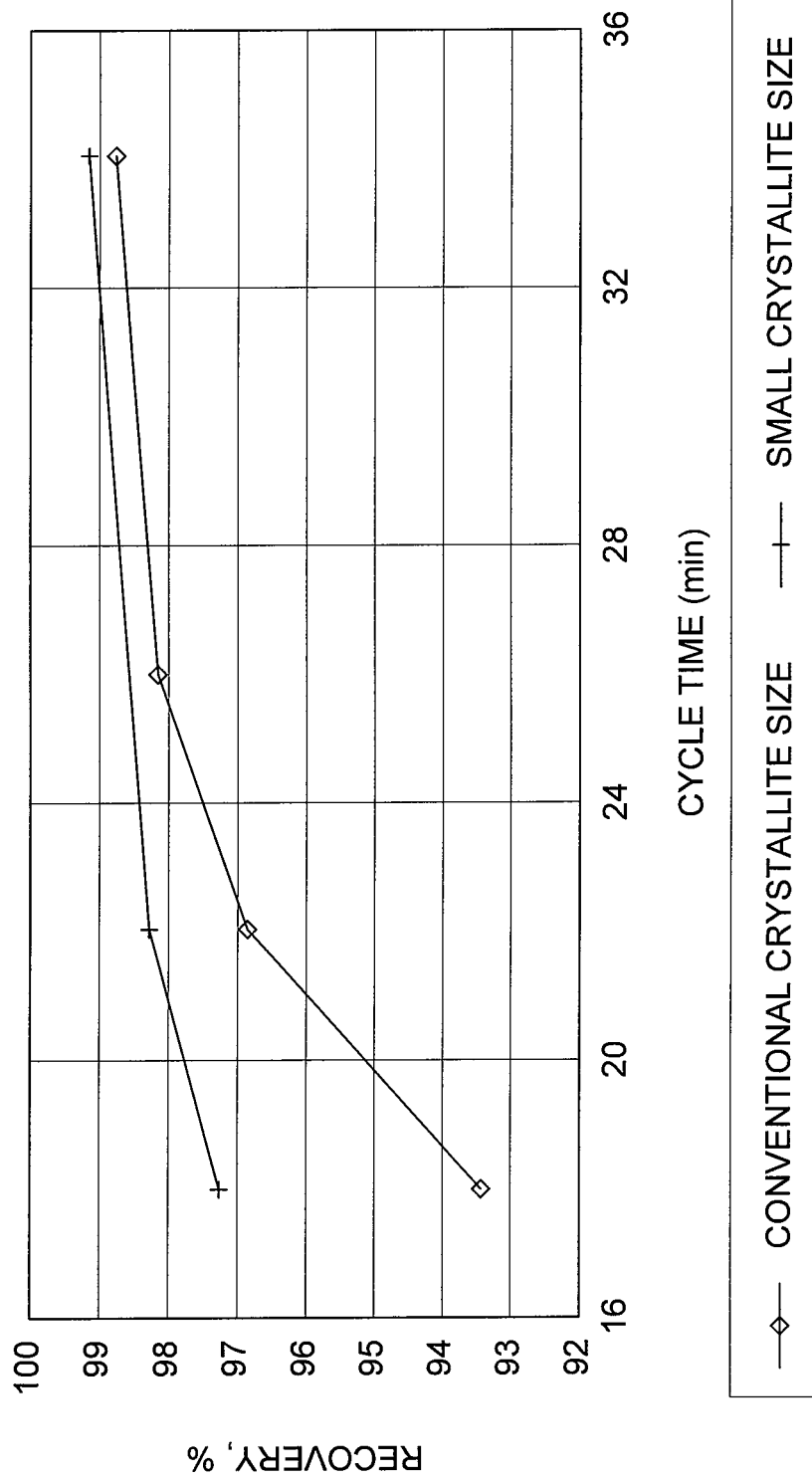
FIG. 5 shows the effect of cycle time on para-xylene recovery, in a para-xylene adsorptive separation process operating in a simulated moving bed mode, for an adsorbent comprising conventional zeolite X crystallites and another adsorbent comprising small-crystallite-size zeolite X, as described above.
Figure 6:
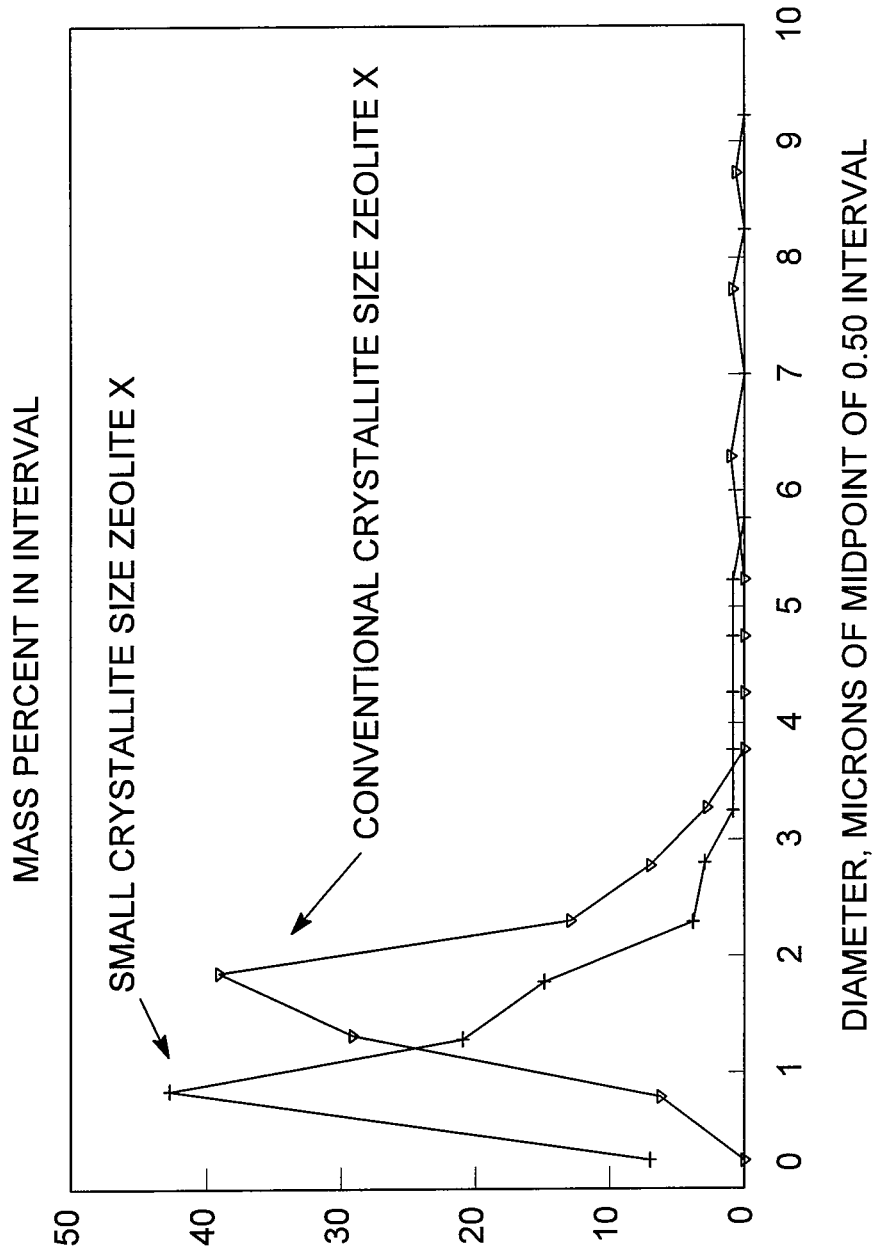
FIG. 6 shows the size distribution of both conventional zeolite X crystallites and zeolite X crystallites having a reduced size.

Use of Adsorbent Comprising Small-Crystallite-Size Zeolite X to Improve Adsorptive Separation of Para-Xylene in Simulated Moving Bed Mode FIG. 5 compares the performance of a conventional adsorbent comprising zeolite X, having an average crystallite of size 1.8-2.0 microns, to an adsorbent comprising zeolite X, having an average crystallite size of 1.4 microns. The zeolite X crystallite size distributions, for a representative conventional zeolite X sample and another sample having the reduced crystallite size, such as those used in the tested adsorbents, are illustrated in FIG. 6, with the average crystallite size for the conventional zeolite X being 1.8-2.0 microns. While maintaining all other conditions constant in a para-xylene adsorptive separation process operating an a simulated moving bed mode, the adsorbent comprising small-crystallite-size zeolite X allowed for a higher overall para-xylene recovery. The advantages associated with the small crystallite size zeolite X, related to the improved adsorbent mass transfer characteristics, became more pronounced as cycle time was reduced, for the reasons discussed above, and as demonstrated in FIG. 5.

Thus, the reduction in zeolite X crystallite size in adsorbents provided a shortened mass transfer path, and consequently an improved mass transfer rate. This has important commercial implications, as para-xylene producers strive to improve productivity by reducing cycle time in adsorptive separation processes operating in simulated moving bed mode. For example, many commercial operations are conducted using 30- or even 27-minute cycle times.

In these cases, the use of adsorbents comprising small-crystallite-size zeolite X is especially advantageous in overcoming mass transfer rate limitations observed for operating temperatures of less than about 175° C. (350° F.). Small-crystallite-size zeolite X has been synthesized with average crystallite sizes in the range from about 0.5 microns (500 nanometers) to about 1.4 microns, which allows for optimization of the zeolite crystallite size for a given application, and consequently the adsorbent formulation and overall process.

The invention claimed is:

1. A simulated moving bed process for separating para-xylene from a mixture comprising at least one other C8 alkylaromatic hydrocarbon, the process comprising contacting, under adsorption conditions, the mixture with an adsorbent comprising zeolite X having an average crystallite size of between 1.4 and less than 1.8 microns to adsorb para-xylene, present in an adsorbed phase, in preference to the at least one other C8 alkylaromatic hydrocarbon present in a non-adsorbed phase; flushing the non-adsorbed phase from contact with the adsorbent to produce a raffinate stream comprising the at least one other C8 alkylaromatic hydrocarbon; and desorbing para-xylene in the adsorbed phase from the adsorbent to produce an extract stream comprising para-xylene; wherein the process has a cycle time from about 18 minutes to about 26 minutes, and recovering at least about 95% of the para-xylene from the mixture.

2. The process of claim 1, wherein the adsorption conditions include an adsorption temperature of less than about 175° C. (350° F.).

3. The process of claim 2, wherein the adsorption conditions include an adsorption temperature from about 150° C. (300° F.) to about 175° C. (350° F.).

4. The process of claim 1, wherein the adsorption conditions include an adsorption pressure from about 1 barg (15 psig) to about 40 barg (580 psig).

5. The process of claim 1, wherein the adsorbent comprises a binder comprising a material selected from the group consisting of clay, alumina, silica, zirconia, and mixtures thereof.

6. The process of claim 5, wherein the binder is present in an amount from about 10% to about 40% by weight, relative to the adsorbent.

7. The process of claim 1, wherein the adsorbent has a water content corresponding to a Loss on Ignition from about 4% to about 7% by weight.

8. The process of claim 1, wherein the zeolite X has at least 95% of its ion-exchangeable sites exchanged with barium or a combination of barium and potassium.

9. The process of claim 1, wherein the mixture comprises ortho-xylene, meta-xylene, para-xylene, and ethylbenzene.

10. The process of claim 9, wherein contacting the mixture with the adsorbent effects adsorption of para-xylene, present in the adsorbed phase, in preference to ortho-xylene, meta-xylene, and ethylbenzene, present in the non-adsorbed phase.

11. The process of claim 10, wherein para-xylene in the adsorbed phase is desorbed into the extract stream comprising a desorbent and the non-adsorbed phase is flushed into the raffinate stream comprising the desorbent.

12. The process of claim 11, wherein the desorbent comprises an aromatic ring-containing compound selected from the group consisting of toluene, benzene, indan, para-diethylbenzene, 1,4-diisopropylbenzene, and mixtures thereof.

13. A process for separating para-xylene from a mixture comprising ortho-xylene, meta-xylene, para-xylene, and ethylbenzene, wherein the process is performed in a simulated moving bed mode and comprises:
    charging a feed stream comprising the mixture and a desorbent stream into one or more vessels comprising an adsorbent comprising zeolite X having an average crystallite size of between 1.4 and less than 1.8 microns to adsorb para-xylene, present in an adsorbed phase, in preference to ortho-xylene, meta-xylene, and ethylbenzene present in a non-adsorbed phase,
    desorbing para-xylene in the adsorbed phase into an extract stream comprising the desorbent,
    flushing the non-adsorbed phase into a raffinate stream comprising the desorbent,
    removing the extract stream and the raffinate stream from the bed of the adsorbent, and
    recovering at least about 95% of the para-xylene from the feed stream,
    wherein the process has a cycle time from about 18 minutes to about 26 minutes and is performed at a temperature of less than about 175° C. (350° F.).

14. The process of claim 13, wherein the zeolite X has a SiO2/Al2O3 framework molar ratio from about 2.0 to about 3.0.

15. The process of claim 13, wherein water is added to either the feed stream or the desorbent stream to obtain a water content in the extract or raffinate stream from about 20 ppm by weight to about 120 ppm by weight.

* * * * *